United States Patent
Chassot et al.

(10) Patent No.: US 6,997,961 B2
(45) Date of Patent: *Feb. 14, 2006

(54) N-HETEROARYLMETHYL-M-PHENYLENEDIAMINE DERIVATIVES-CONTAINING DYES FOR KERATIN FIBERS AND NOVEL N-HETEROARYLMETHYL-M-PHENYLENEDIAMINE DERIVATIVES

(75) Inventors: Laurent Chassot, Praroman (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 427 days.

This patent is subject to a terminal disclaimer.

(21) Appl. No.: 10/258,692

(22) PCT Filed: Oct. 18, 2001

(86) PCT No.: PCT/EP01/12053

§ 371 (c)(1),
(2), (4) Date: Oct. 25, 2002

(87) PCT Pub. No.: WO02/072568

PCT Pub. Date: Sep. 19, 2002

(65) Prior Publication Data

US 2005/0081310 A1     Apr. 21, 2005

(30) Foreign Application Priority Data

Mar. 13, 2001  (DE) ................. 101 11 936

(51) Int. Cl.
*A61K 7/13* (2006.01)
(52) U.S. Cl. ............... 8/405; 8/406; 8/410; 8/411; 8/412; 8/416; 8/423; 8/570; 8/571; 8/572; 8/575; 8/577; 548/127; 548/131; 548/356.1; 548/300.1
(58) Field of Classification Search ......... 8/405, 8/408, 410, 411, 412, 416, 423, 570, 571, 8/572, 575, 577; 548/758, 127, 131, 300.1, 548/356.1; 549/200
See application file for complete search history.

(56) References Cited

U.S. PATENT DOCUMENTS

| 4,325,704 A | 4/1982 | Konrad et al. ......... 8/407 |
| 6,600,050 B1 * | 7/2003 | Chassot et al. ......... 548/364.4 |

FOREIGN PATENT DOCUMENTS

| DE | 28 27 658 A | 1/1979 |
| DE | 29 34 330 A1 | 3/1981 |
| EP | 0 024 660 A | 3/1981 |
| EP | 0 761 214 A | 3/1997 |
| EP | 0 963 982 A | 12/1999 |

OTHER PUBLICATIONS

STIC Search Report (Feb. 18, 2005).*
IZV. AKAD. NAUK. SSR, SER. KHIM (1967), (9), PP. 2049-2055.

* cited by examiner

*Primary Examiner*—Eisa Elhilo
(74) *Attorney, Agent, or Firm*—Michael J. Striker

(57) ABSTRACT

Dyeing agents for keratin fibers, containing N-heteroarylmethyl-m-phenylenediamine derivatives of general formula (I) or the salts thereof

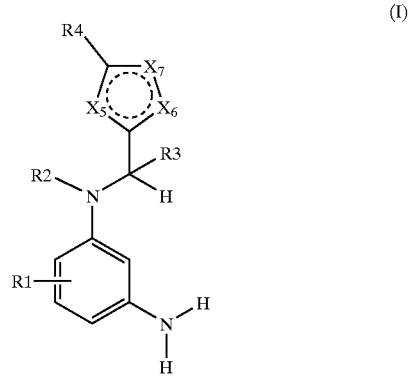

and new N-heteroarylmethyl-m-phenylenediamine derivatives.

15 Claims, No Drawings

N-HETEROARYLMETHYL-M-PHENYLENEDIAMINE DERIVATIVES-CONTAINING DYES FOR KERATIN FIBERS AND NOVEL N-HETEROARYLMETHYL-M-PHENYLENEDIAMINE DERIVATIVES

BACKGROUND OF THE INVENTION

1. Field of the Invention.

The present invention relates to agents for oxidative dyeing of keratin fibers, particularly human hair, based on a developer/coupler combination which contains an N-heteroarylmethyl-m-phenylenediamine derivative as the coupler, and to new N-heteroarylmethyl-m-phenylenediamine derivatives.

2. Description of the Related Art

In the area of keratin fiber dyeing, particularly hair dyeing, oxidation dyes have attained substantial importance. In this case, the coloration is produced by reaction of certain developers with certain couplers in the presence of an appropriate oxidant. Suitable developers are, in particular, 2,5-diaminotoluene, 2,5-diaminophenylethyl alcohol, p-aminophenol, 1,4-diaminobenzene and 4,5-diamino-1-(2-hydroxyethyl)-pyrazole, and suitable couplers are, for example, resorcinol, 2-methylresorcinol, 1-naphthol, 3-aminophenol, m-phenylenediamine, 2-amino-4-(2'-hydroxyethyl)amino-anisole, 1,3-diamino-4-(2'-hydroxyethoxy)benzene and 2,4-diamino-5-fluorotoluene.

The oxidation dyes used for dyeing human hair must meet numerous requirements in addition to that of being able to produce colorations of the desired intensity. For example, these dyes must be harmless from a toxicological and dermatological standpoint, and the hair colorations obtained must have good light fastness, resistance to permanent waving, acid fastness and rubbing fastness. In any case, however, in the absence of exposure to light, rubbing and chemicals, such colorations must remain stable over a period of at least 4 to 6 weeks. Moreover, by combining appropriate developers and couplers, it must be possible to create a wide range of different color shades.

Attempts have already been made to improve the properties of m-phenylenediamines by introduction of substituents. In this regard, the reader is referred to German Unexamined Patent Application DE 29 34 330 which, among other things, describes special N-substituted m-phenylenediamines as couplers. With the currently known dyeing agents, however, it is not possible to meet the requirements placed on dyeing agents in all respects.

SUMMARY OF THE INVENTION

Hence, the need continued to exist for novel couplers that would meet the aforesaid requirements to a particularly high degree.

We have now found that intense, stable violet to dark-blue color shades can be obtained by use of special N-heteroarylmethyl-m-phenylenediamine derivatives of general formula (I).

Hence, the object of the present invention is an agent for oxidative dyeing of keratin fibers, for example wool, furs, feathers or hair, particularly human hair, which agent is based on a developer-coupler combination characterized by the fact that it contains as the coupler at least one N-heteroarylmethyl-m-phenylenediamine derivative of formula (I) or a salt thereof with an organic or inorganic acid

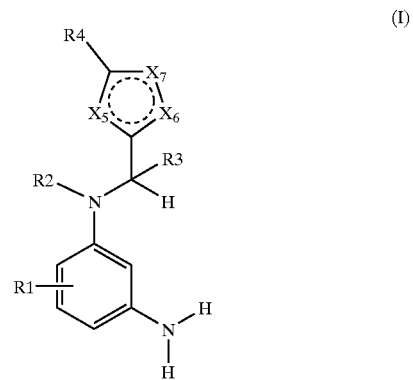

wherein
X5 denotes sulfur, nitrogen, oxygen, C—R6 or N—R5;
X6 denotes sulfur, nitrogen, oxygen, C—R7 or N—R5;
X7 denotes sulfur, nitrogen, oxygen, C—R8 or N—R5;
R1 denotes hydrogen, a $C_1$–$C_4$-alkyl group, a $C_1$–$C_4$-hydroxyalkoxy group or $C_1$–$C_4$-hydroxyalkyl group;
R2 and R3 can be equal or different and independently of each other denote hydrogen or a $C_1$–$C_8$-alkyl group;
R4, R6, R7, R8 can be equal or different and independently of each other denote hydrogen, a halogen atom (F, Cl, Br, I), a cyano group, a $C_1$–$C_4$-alkoxy group, a $C_1$–$C_6$-alkyl group, a $C_1$–$C_4$-alkyl thioether group, a mercapto group, a nitro group, an amino group, a $C_1$–$C_4$-alkylamino group, a di($C_1$–$C_4$)-alkylamino group, a di($C_1$–$C_4$-hydroxyalkyl)amino group, a $C_1$–$C_4$-hydroxyalkylamino group, a trifluoromethyl group, a —C(O)CH$_3$— group, a —C(O)CF$_3$ group, an —Si(CH$_3$)$_3$ group, a $C_1$–$C_4$-hydroxyalkyl group or a $C_3$–$C_4$ dihydroxyalkyl group; and
R5 denotes hydrogen, a $C_1$–$C_6$-alkyl group, a $C_2$–$C_4$-hydroxyalkyl group, a phenyl group or an acetyl group; at least one and at the most two of the X5 to X7 groups denoting respectively C—R6 or C—R7 or C—R8 and at the most one of the X5 to X7 groups denoting sulfur, oxygen or N—R5.

Noteworthy among the compounds of formula (I) are, for example: N-thiophen-3-ylmethyl-1,3-diaminobenzene, N-furan-3-ylmethyl-1,3-diaminobenzene, N-(1H-imidazol-2-ylmethyl)-1,3-diaminobenzene, N-(1H-pyrol-2-ylmethyl)-1,3-diaminobenzene, N-thiophen-2-ylmethyl-1,3-diaminobenzene, N-thiazol-2-yl-methyl-1,3-diaminobenzene, N-(5-nitrothiophen-2-ylmethyl)-1,3-diaminobenzene, N-(3-methylthiophen-2-ylmethyl)-1,3-diaminobenzene, N-(2-methylthiophen-3-ylmethyl)-1,3-diaminobenzene, N-(4-methylthiophen-3-ylmethyl)-1,3-diaminobenzene, N-(5-methylthiophen-2-ylmethyl)-1,3-diaminobenzene, N-(3-chlorothiophen-2-ylmethyl)-1,3-diaminobenzene, N-(4-methylthiophen-2-ylmethyl)-1,3-diaminobenzene, N-(4-chlorothiophen-2-ylmethyl)-1,3-diaminobenzene, N-(5-methylthiophen-2-ylmethyl)-1,3-diaminobenzene, N-(5-chlorothiophen-2-ylmethyl)-1,3-diaminobenzene, 2-{4-amino-2-[(furan-2-ylmethyl)amino]phenoxy}ethanol, 2-{4-amino-2-[(thiophen-3-ylmethyl)amino]phenoxy}ethanol, 2-{4-amino-2-[(thiophen-2-ylmethyl)amino]phenoxy}ethanol, 2-{4-amino-2-[(1H-imidazol-2-ylmethyl)amino]phenoxy}ethanol, 2-{4-amino-2-[(furan-3-ylmethyl)amino]phenoxy}ethanol, 2-{4-amino-2-[(1H-pyrol-2-ylmethyl)amino]phenoxy}ethanol, 2-{4-amino-2-[(3-methylthiophen-2-ylmethyl)amino]phenoxy}ethanol, 2-{4- amino-2-[(3-chlorothiophen-2-ylmethyl)amino]
phenoxy}ethanol, 2-{4-amino-2-[(4-methylthiophen-2-ylmethyl)amino]phenoxy}ethanol, 2-{4-amino-2-[(4-chlorothiophen-2-ylmethyl)amino]phenoxy}ethanol, 2-{4-amino-2-[(5-chlorothiophen-2-ylmethyl)amino]
phenoxy}ethanol, 2-{4-amino-2-[(5-methylthiophen-2-ylmethyl)amino]phenoxy}ethanol, 2-{4-amino-2-[(2-methylthiophen-3-ylmethyl)amino]phenoxy}ethanol, 2-{4-amino-2-[(2-chlorothiophen-3-ylmethyl)amino]
phenoxy}ethanol, 2-{4-amino-2-[(4-methylthiophen-3-ylmethyl)amino]phenoxy}ethanol, 2-{4-amino-2-[(4-chlorothiophen-3-ylmethyl)amino]phenoxy}ethanol, 2-{4-amino-2-[(5-methylthiophen-3-ylmethyl)amino]
phenoxy}ethanol, 2-{4-amino-2-[(5-chlorothiophen-3-ylmethyl)amino]phenoxy}ethanol, 2-{2-amino-4-[(furan-2-ylmethyl)amino]phenoxy}ethanol, 2-{2-amino-4-[(thiophen-3-ylmethyl)amino]phenoxy}ethanol, 2-{2-amino-4-[(thiophen-2-ylmethyl)amino]phenoxy}ethanol, 2-{2-amino-4-[(1H-imidazol-2-ylmethyl)amino]
phenoxy}ethanol and 2-{2-amino-4-[(furan-3-ylmethyl)amino]phenoxy}ethanol.

Preferred compounds of formula (I) are those wherein (i) R1 denotes hydrogen or a hydroxyalkoxy group and R2 and R3 or R2, R3 and R4 denote hydrogen; or (ii) R1 denotes hydrogen or a hydroxyalkoxy group and the R2 and R3 groups or the R2, R3 and R4 groups denote hydrogen, X5 denotes sulfur or oxygen, X6 denotes nitrogen or C—R7 and X7 denotes C—R8, with at least one of the R7 and R8 groups denoting hydrogen; or (iii) R1 denotes hydrogen or a hydroxyalkoxy group, the R2 and R3 groups or the R2, R3 and R4 groups denote hydrogen, X7 denotes sulfur or oxygen, X5 denotes C—R6 and X6 denotes C—R7, with at least one of the R6 and R7 groups denoting hydrogen; or (iv) R1 denotes hydrogen or a hydroxyalkoxy group, the R2 and R3 groups or the R2, R3 and R4 groups denote hydrogen, X6 denotes sulfur or oxygen, X5 denotes C—R6 and X7 denotes C—R8, with at least one of the R6 and R8 groups denoting hydrogen.

Particularly preferred are the following N-heteroarylmethyl-m-phenylenediamine derivatives of formula (I): N-thiophen-3-ylmethyl-1,3-diaminobenzene, N-furan-3-ylmethyl-1,3-diaminobenzene, N-furan-2-ylmethyl-1,3-diaminobenzene, N-thiophen-2-ylmethyl-1,3-diaminobenzene, 2-{4-amino-2-[(thiophen-3-ylmethyl)amino]phenoxy}ethanol, 2-{4-amino-2-[(thiophen-2-ylmethyl)amino]phenoxy}-ethanol, 2-{4-amino-2-[(furan-3-ylmethyl)amino]phenoxy}ethanol, 2-{4-amino-2-[(furan-2-ylmethyl)-amino]phenoxy}ethanol, 2-{2-amino-4-[(thiophen-2-ylmethyl)amino]phenoxy}ethanol and 2-{2-amino-4-[(furan-2-ylmethyl)amino]phenoxy}ethanol, or the salts thereof.

The compounds of formula (I) can be used as the free bases as well as in the form of their physiologically tolerated salts with inorganic or organic acids, for example hydrochloric acid, sulfuric acid, phosphoric acid, acetic acid, propionic acid, lactic acid or citric acid.

The colorant of the invention contains the N-heteroarylmethyl-m-phenylenediamine derivatives of formula (I) in a total amount from about 0.005 to 20 wt. %, an amount of about 0.01 to 5 wt. % and especially 0.1 to 2.5 wt. % being preferred.

Suitable developers are all those developers that are known to be used with, and are appropriate for, such colorants, for example 1,4-diaminobenzene (p-phenyl-ene-diamine), 1,4-diamino-2-methylbenzene (p-toluylenediamine), 1,4-diamino-2,6-dimethylbenzene, 1,4-diamino-3,5-diethyl-benzene, 1,4-diamino-2,5-dimethyl-benzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)benzene, 1-(2,5-diaminophenyl) ethanol, 2-[2-(acetylamino)ethoxy)]-1,4-diaminobenzene, 4-phenylaminoaniline, 4-dimethylaminoaniline, 4-diethylaminoaniline, 4-dipropylaminoaniline, 4-[ethyl-(2-hydroxyethyl)amino]aniline, 4-[di(2-hydroxyethyl)amino] aniline, 4-[di(2-hydroxyethyl)amino]-2-methylaniline, 4-[(2-methoxyethyl)amino]aniline, 4-[(3-hydroxypropyl) amino]-aniline, 4-[(2,3-dihydroxypropyl)amino]aniline, 1,4-diamino-2-(2-hydroxyethyl)-benzene, 1,4-diamino-2-(1-methylethyl)benzene, 1,3-bis-[(4-aminophenyl)-(2-hydroxyethyl)amino]-2-propanol, 1,4-bis-[(4-aminophenyl) amino]butane, 1,8-bis-(2,5-diaminophenoxy)-3,6-dioxaoctane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4amino-2-[(2-hydroxyethyl)amino]methylphenol, 4-amino-2-methylphenol, 4amino-2-(methoxymethyl)phenol, 4-amino-2-(2-hydroxyethyl)phenol, 5-aminosalicylic acid, 2,5-diaminopyridine, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 4,5-diamino-3-methyl-1-methyl-1H-pyrazole, 2-aminophenol, 2-amino-6-methylphenol and 2-amino-5-methylphenol.

Moreover, the colorant of the invention can optionally also contain other known couplers, for example 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di(2-hydroxyethoxy) benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino] aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino] aniline, 1,3-di(2,4-diaminophenoxy)propane di(2,4-diaminophenoxy)methane, 1,3-diamino-2,4-dimethoxybenzene, 2,6-bis-(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-2-methylphenol, 3-[(2-hydroxyethyl) amino]phenol, 3-[(2-methoxyethyl)amino]phenol, 5-amino-2-ethylphenol, 2-(4-amino-2-hydroxyphenoxy)-ethanol, 5-[(3-hydroxypropyl)amino]-2-methylphenol, 3-[(2,3-dihydroxypropyl)amino]-2-methylphenol, 3-[(2-hydroxyethyl) amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

The couplers and developers can be present in the colorant of the invention either individually or in admixture with one another, the total amount of each of the couplers and developers in the colorant of the invention being about 0.005 to 20 wt. % preferably about 0.01 to 5.0 wt. % and particularly 0.1 to 2.5 wt. % (based on the total amount of colorant). The total amount of the developer-coupler combination contained in the colorant described herein is preferably about-0.01 to 20 wt. %, an amount of about 0.02 to 10 wt. % and especially 0.2 to 6 wt. % being particularly preferred. In general, the developers and couplers are used in approximately equimolar amounts. In this respect, it is not disadvantageous, however, if the developers are present in a certain excess or deficiency [for example in a (coupler: developer) ratio of 1:2 to 1:0.5].

The couplers and developers can be present in the colorant of the invention either individually or in admixture with one another, the total amount of each of the couplers and developers in the colorant of the invention being about 0.005 to 20 wt. % preferably about 0.01 to 5.0 wt. % and particularly 0.1 to 2.5 wt. % (based on the total amount of colorant). The total amount of the developer-coupler combination contained in the colorant described herein is preferably about 0.01 to 20 wt. %, an amount of about 0.02 to 10 wt. % and especially 0.2 to 6 wt. % being particularly preferred. In general, the developer and the coupler are used in approximately equimolar amounts. In this respect, it is not disadvantageous, however, if the developer is present in a certain excess or deficiency [for example in a (coupler: developer) ratio of 1:2 to 1:0.5].

Moreover, the colorant of the invention can also contain other dye components, for example 6-amino-2-methylphenol and 2-amino-5-methylphenol, as well as common anionic, cationic, amphoteric or nonionic direct dyes, for example triphenylmethane dyes such as 4-[(4'-aminophenyl)-(4'-imino-2",5"-cyclohexadien-1"-ylidene)methyl]-2-methylaminobenzene monohydrochloride (Color Index [C.I.] 42 510) and 4-[(4'-amino-3'-methylphenyl)-4"-imino-3"-methyl-2",5"-cyclohexadien-1"-ylidene)methyl]-2-methylaminobenzene monohydrochloride (C.I. 42 520); aromatic nitro dyes such as 4-(2'-hydroxyethyl)amino-nitrotoluene, 2-amino-4,6-dinitrophenol, 2-amino-5-(2'-hydroxyethyl)amino-nitrobenzene, 2-chloro-6-(ethylamino)-4-nitrophenol, 4-chloro-N-(2-hydroxyethyl)-2-nitroaniline, 5-chloro-2-hydroxy-4-nitroaniline, 2-amino-4-chloro-6-nitrophenol and 1-(2'-ureidoethyl)amino-4-nitrobenzene; azo dyes such as sodium 6-[(4'-aminophenyl)azo]-5-hydroxynaphthalene-1-sulfonate (C.I. 14 805) and disperse dyes, for example 1,4-diaminoanthraquinone and 1,4,5,8-tetraamino-anthraquinone. The colorants of the invention can contain the aforesaid dye components in an amount from about 0.1 to 4 wt. %.

The couplers and developers as well as the other dye components, provided they are bases, can, of course, also be used in the form of their physiologically tolerated salts with organic or inorganic acids, for example hydrochloric acid or sulfuric acid, or—if they contain aromatic OH groups—in the form of their salts with bases, for example as alkali metal phenoxides.

Moreover, if the colorants of the invention are to be used for coloring hair, they can also contain other common cosmetic additives, for example antioxidants such as ascorbic acid, thioglycolic acid or sodium sulfite, as well as perfume oils, complexing agents, wetting agents, emulsifiers, thickeners and hair-care agents.

The colorant of the invention can be in the form of, for example, a solution, particularly an aqueous or aqueous-alcoholic solution. A particularly preferred formulation form, however, is a cream, gel or emulsion. Such a composition consists of a mixture of the dye components and the usual additives employed for such compositions.

Common additives to solutions, creams, emulsions or gels are, for example solvents such as water, lower aliphatic alcohols, for example ethanol, propanol or isopropanol, glycerol or glycols such as 1,2-propylene glycol, moreover wetting agents or emulsifiers from the classes of anionic, cationic, amphoteric or nonionic surface-active agents, for example fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides and ethoxylated fatty esters, furthermore thickeners such as the higher fatty alcohols, starch, cellulose derivatives, petrolatum, paraffin oil and fatty acids, also hair-care agents such as cationic resins, lanolin derivatives, cholesterol, pantothenic acid and betaine. The said constituents are used in amounts commonly employed for such purposes, for example the wetting agents and emulsifiers at a concentration of about 0.5 to 30 wt. %, the thickeners in an amount from about 0.1 to 25 wt. % and the hair-care agents at a concentration from about 0.1 to 5 wt. %.

The ready-to-use hair colorant of the invention is prepared by mixing the colorant with an oxidant just before use.

Suitable oxidants are primarily hydrogen peroxide or its products of addition to urea, melamine, sodium borate or sodium carbonate in the form of a 1 to 12% and preferably 3 to 6% aqueous solution. The weight ratio of hair colorant to oxidant in this case is preferably from 5:1 to 1:3 and particularly from 1:1 to 1:2. Higher amounts of oxidant are used especially with higher concentrations of hair colorant or when stronger bleaching of the hair is wanted at the same time. In principle, however, atmospheric oxygen can be used in place of the aforesaid oxidants to oxidize the dyes.

During the mixing of the dye (the pH of which is approximately 6 to 11.5) with the oxidant, which most frequently is adjusted to an acidic pH (approximately 2 to 6.5), the pH of the ready-to-use hair colorant of the invention assumes a value which depends on the amount of alkali in the dye and of acid in the oxidant as well as on the mixing ratio. Depending on the composition, the colorant of the invention can be weakly acidic, neutral or alkaline and in the ready-to-use form can have a pH of about 3 to 11.5 and preferably about 6 to 10. The adjustment to a basic pH is preferably made with ammonia, but it can also be made with an organic amine, for example with 2-amino-2-methyl-1-propanol, tris(hydroxymethyl)aminomethane, monoethanolamine and triethanolamine, or with an inorganic base such as sodium hydroxide and potassium hydroxide. The adjustment to an acidic pH can be made with an inorganic or organic acid, for example phosphoric, acetic, lactic, ascorbic, citric or tartaric acid.

Then, depending on the hair fullness, an amount of this mixture sufficient for the hair treatment, usually about 60 to 200 grams, is applied to the hair, and the mixture is allowed to act on the hair at about 15 to 50° C. and preferably at 30 to 40° C., for about 10 to 45 min and preferably for 30 min after which the hair is rinsed with water and dried. Optionally, following this rinsing the hair is washed with a shampoo and optionally post-rinsed with a weak organic acid, for example citric acid or tartaric acid. The hair is then dried.

The colorants of the invention containing an N-heteroarylmethyl-m-phenylenediamine derivative of formula (I) as coupler give hair colorations of excellent color stability, particularly in terms of light fastness, wash fastness and rubbing fastness. As far as the dyeing properties are concerned, the hair colorants of the invention provide a wide range of different color shades from blond to brown, purple, violet and even blue and black, depending on the kind and composition of the dye components used, the achievable violet to dark-blue shades being particularly noteworthy. The color shades are characterized by their unusual color intensity. The very good coloring properties of the hair colorant of the present patent application also manifest themselves particularly in that this colorant makes it possible to dye gray hair, previously not damaged chemically, without any problems and with good covering power.

The N-heteroarylmethyl-m-phenylenediamine derivatives of formula (I) of the invention can be prepared by known methods of synthesis, for example by the methods described in the practical examples given hereinbelow.

The N-heteroarylmethyl-m-phenylenediamine derivatives of formula (I) are highly water-soluble and give colorations of high color intensity and excellent color stability, particularly in terms of light fastness, wash fastness and rubbing fastness. Moreover, they have excellent storage stability, particularly as constituents of the oxidation colorants described herein.

Hence, another object of the present invention are N-heteroarylmethyl-m-phenylenediamine derivatives of general formula (II) or the water-soluble salts thereof with organic or inorganic acids

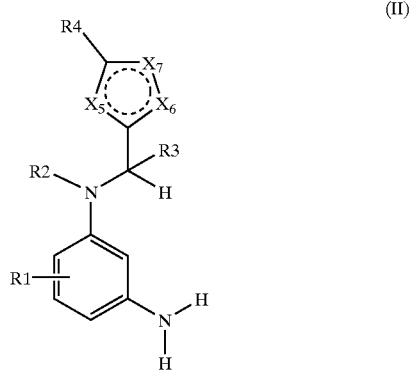

(II)

wherein
X5 denotes sulfur, nitrogen, oxygen, C—R6 or N—R5;
X6 denotes sulfur, nitrogen, oxygen, C—R7 or N—R5;
X7 denotes sulfur, nitrogen, oxygen, C—R8 or N—R5;
R1 denotes hydrogen, a $C_1$–$C_4$-alkyl group, a $C_1$–$C_4$-hydroxyalkoxy group or a $C_1$–$C_4$-hydroxyalkyl group;
R2 and R3 can be equal or different and independently of each other denote hydrogen or a $C_1$–$C_6$-alkyl group;

R4, R6, R7, R8 can be equal or different and independently of each other denote hydrogen, a halogen atom (F, Cl, Br, I), a cyano group, a $C_1$–$C_4$-alkoxy group, a $C_1$–$C_6$-alkyl group, a $C_1$–$C_4$-alkyl thioether group, a mercapto group, a nitro group, an amino group, a $C_1$–$C_4$-alkylamino group, a di($C_1$–$C_4$)-alkylamino group, a di($C_1$–$C_4$-hydroxyalkyl)amino group, a $C_1$–$C_4$-hydroxyalkylamino group, a trifluoromethyl group, a —C(O)CH$_3$— group, a —C(O)CF$_3$ group, an —Si(CH$_3$)$_3$ group, a $C_1$–$C_4$-hydroxyalkyl group or a $C_3$–$C_4$ dihydroxyalkyl group; and
R5 denotes hydrogen, a $C_1$–$C_6$-alkyl group, a $C_2$–$C_4$-hydroxyalkyl group, a phenyl group or an acetyl group; at least one and at the most two of the X5 to X7 groups denoting respectively C—R6 or C—R7 or C—R8 and at the most one of the X5 to X7 groups denoting sulfur, oxygen or N—R5;
provided that at least one of the R1, R2, R3, R4, R6, R7 and R8 groups does not denote hydrogen when X5 or X6 denotes sulfur.

The following examples illustrate the object of the invention in greater detail without limiting its scope.

EXAMPLES

Example 1

Synthesis of N-heteroarylmethyl-1,3-diaminobenzenes

A. Synthesis of tert.butyl (3-aminophenyl)carbamate

A solution of 11 g (50 mmol) of ditert.butyl dicarbonate in 30 mL of methylene chloride was added dropwise to a solution of 10.8 g (100 mmol) of 1,3-phenylenediamine in 100 mL of methylene chloride/NaOH (4%) 1:1. The reaction mixture was allowed to agitate 8 hours after which 5 g of ditert.butyl dicarbonate was added to it. The reaction mixture was then allowed to agitate for an additional 12 hours at room temperature. The organic phase was washed with a saturated aqueous sodium chloride solution, dried over sodium sulfate and filtered, and the filtrate was evaporated. The resulting crude product was purified on silica gel with hexane/ethyl acetate (1:1). This gave 6.2 g (30% of the theoretical) of tert.butyl (3-aminophenyl)carbamate.

$^1$H-NMR (300 MHz, CDCl$_3$): δ=7.06 (t, 1H); 6.99 (br s, 1H); 6.44 (br s, 2H); 6.56 (d, 1H); 6.39 (m, 2H); 3.68 (br, 2H); 1.53 (s, 9H).

B. Synthesis of N-heteroarylmethyl-1.3-diaminobenzenes 0.031 g (0.15 mmol) of tert.butyl (3-aminophenyl)carbamate from step 1A and 0.1 mmol of the appropriate aldehyde were dissolved in methanol (dried over molecular sieve). 10 mg of molecular sieve was added, and the reaction mixture was allowed to agitate for 7 hours. Then, 0.3 mL of a borane-tetrahydrofuran complex solution (1M in tetrahydrofuran) was added at 0° C., and the reaction mixture was allowed to agitate for one hour at room temperature. At the end of the reaction, the reaction mixture was poured into water and extracted with ethyl acetate. The organic phase was dried with magnesium sulfate, the solvent was distilled off in a rotary evaporator and the residue was purified on silica gel with petroleum ether/ethyl acetate (1:1). The resulting product in 4 mL of ethanol and 1.5 mL of a 2.9-molar ethanolic hydrochloric acid solution was heated to 50° C. The resulting precipitate was filtered off, washed twice with 1-mL portions of ethanol and then dried.

a. N-Thiophen-2-ylmethyl-1,3-diaminobenzene hydrochloride
Aldehyde derivative used: thiophene-2-carbaldehyde
Mass spectrum: MH$^+$ 203 (100)

b. N-Thiophen-3-ylmethyl-1.3-diaminobenzene hydrochloride
Aldehyde derivative used: thiophene-3-carbaldehyde
Mass spectrum: $MH^+$ 205 (100)

c. N-Furan-2-ylmethyl-1,3-diaminobenzene hydrochloride
Aldehyde derivative used: furan-2-carbaldehyde
Mass spectrum: $MH^+$ 189 (100)

d. N-Furan-3-ylmethyl-1,3-diaminobenzene hydrochloride
Aldehyde derivative used: furan-3-carbaldehyde
Mass spectrum: $MH^+$ 189 (100)

e. N-(1H-Imidazol-2-ylmethyl)-1.3-diaminobenzene hydrochloride
Aldehyde derivative used: imidazole-2-carbaldehyde
Mass spectrum: $MH^+$ 189 (100)

f. N-Thiazol-2-ylmethyl-1,3-diaminobenzene hydrochloride
Aldehyde derivative used: thiazole-2-carbaldehyde
Mass spectrum: $MH^+$ 242 (100)

g. N-(5-Nitrothiophen-2-ylmethyl)-1,3-diaminobenzene hydrochloride
Aldehyde derivative used: 5-nitrothiophene-2-carbaldehyde
Mass spectrum: $MH^+$ 250 (20).

Example 2

Synthesis of 2-{4-amino-2-[(N-heteroarylmethyl)amino]-phenoxy}ethanols

A. Synthesis of tert.butyl [3-amino-4-(2-hydroxyethoxy)phenyl]carbamate

A solution of 16.8 g of $NaHCO_3$ in 100 mL of water was added dropwise to a solution of 10.7 g (100 mmol) of 2-(2,4-diaminophenoxy)ethanol in 300 mL of acetonitrile. Then, 22 g (100 mmol) of ditert.butyl dicarbonate was added, and the reaction mixture was allowed to agitate for 6 hours. At the end of the reaction, the reaction mixture was poured into 100 mL of dichloromethane, and the organic phase was extracted with dilute hydrochloric acid. The aqueous phase was rendered alkaline with a 2N sodium hydroxide solution [sic—Translator] and then extracted with dichloromethane. The organic phase was dried over sodium sulfate and the solvent was distilled off in a rotary evaporator. This gave 10.3 g (38% of the theoretical) of tert.butyl [3-amino-4-(2-hydroxyethoxy)phenyl]carbamate.

$^1$H-NMR (300 MHz, $CDCl_3$): δ=7.26 (br s, 1H); 6.95 (d, 1H); 6.72 (d, 1H); 6.34 (s, 1H); 4.77 (m, 2H); 3.9 (m, 2H); 1.50 (s, 9H).

B. Synthesis of 2-{4-amino-2-[(N-heteroarylmethyl)amino]phenoxy}ethanols 0.031 g (0.15 mmol) of tert.butyl [3-amino-4-(2-hydroxyethoxy)phenyl]carbamate from Example 2A and 0.1 mmol of the appropriate aldehyde were dissolved in methanol (dried over molecular sieve). 10 mg of molecular sieve was added, and the reaction mixture was allowed to agitate for 7 hours. Then, 0.3 mL of a borane-tetrahydrofuran complex solution (1 M in tetrahydrofuran) was added at 0° C., and the reaction mixture was allowed to agitate for one hour at room temperature. At the end of the reaction, the reaction mixture was poured into water and extracted with ethyl acetate. The organic phase was dried with magnesium sulfate. The solvent was distilled off in a rotary evaporator, and the residue was purified on silica gel with petroleum ether/ethyl acetate (1:1). The resulting product in 4 mL of ethanol and 1.5 mL of a 2.9-molar ethanolic hydrochloric acid solution was heated to 50° C. The precipitate was filtered off, washed twice with 1-mL portions of ethanol and then dried.

a. 2-{4-Amino-2-[(thiophen-2-ylmethyl)amino]phenoxy}ethanol hydrochloride
Aldehyde derivative used: thiophene-2-carbaldehyde
Mass spectrum: $MH^+$ 265 (100)

b. 2-{4-Amino-2-[(furan-2-ylmethyl)amino]phenoxy}ethanol hydrochloride
Aldehyde derivative used: furan-2-carbaldehyde
Mass spectrum: $MH^+$ 249 (100)

c. 2-{4-Amino-2-[(thiophen-3-ylmethyl)amino]phenoxy}ethanol hydrochloride
Aldehyde derivative used: thiophene-3-carbaldehyde
Mass spectrum: $MH^+$ 265 (20)

d. 2-{4-Amino-2-[(1H-imidazol-2-ylmethyl)amino]phenoxy}ethanol hydrochloride
Aldehyde derivative used: imidazole-2-carbaldehyde
Mass spectrum: $MH^+$ 249 (10)

e. 2-{4-Amino-2-[(furan-3-ylmethyl)amino]phenoxy}ethanol hydrochloride
Aldehyde derivative used: furan-3-carbaldehyde
Mass spectrum: $MH^+$ 249 (20)

Examples 3 to 14

Hair Colorants
Hair colorant solutions having the following composition were prepared:

| | |
|---|---|
| 1.25 mmol | of coupler of formula (I) as per Table 1 |
| 1.25 mmol | of developer as per Table 1 |
| 1.0 g | of potassium oleate (8% aqueous solution) |
| 1.0 g | of ammonia (22% aqueous solution) |
| 1.0 g | of ethanol |
| 0.3 g | of ascorbic acid |
| to 100.0 g | water |

Just before use, 50 g of the foregoing coloring solution was mixed with 50 g of a 6% aqueous hydrogen peroxide solution. The mixture was then applied to bleached hair. After an exposure time of 30 min at 40° C., the hair was rinsed with water, washed with a commercial shampoo and dried. The resulting color shades are presented in Table 1.

TABLE 1

| | | Developer | | | |
|---|---|---|---|---|---|
| Example No. | Coupler of formula (I) | I. 1,4-Diamino-benzene | II. 2,5-Diamino-toluene sulfate | III. 2,5-Diamino-phenylethanol sulfate | IV. 4,5-Diamino-1-(2'-hydroxy-ethyl)pyrazole sulfate |
| 3 | As per Ex. 1a | dark blue | dark blue | dark blue | violet |
| 4 | As per Ex. 1b | dark blue | dark blue | dark blue | violet |
| 5 | As per Ex. 1c | dark blue | dark blue | dark blue | violet |

TABLE 1-continued

| Example No. | Coupler of formula (I) | Developer I. 1,4-Di amino- benzene | II. 2,5-Diamino- toluene sulfate | III. 2,5-Diamino- phenylethanol sulfate | IV. 4,5-Diamino-1- (2'-hydroxy- ethyl)pyrazole sulfate |
|---|---|---|---|---|---|
| 6 | As per Ex. 1d | dark blue | dark blue | dark blue | violet |
| 7 | As per Ex. 1e | blue | blue | blue | violet |
| 8 | As per Ex. 1f | blue | blue | blue | violet |
| 9 | As per Ex. 1g | blue | gray-blue | gray-blue | bright violet |
| 10 | As per Ex. 2a | dark blue | dark blue | dark blue | violet |
| 11 | As per Ex. 2b | dark blue | dark blue | dark blue | violet |
| 12 | As per Ex. 2c | dark blue | dark blue | dark blue | violet |
| 13 | As per Ex. 2d | dark blue | dark blue | dark blue | violet |
| 14 | As per Ex. 2e | dark blue | dark blue | dark blue | violet |

Examples 15 to 39

Hair Colorants
Hair colorant solutions of the following composition were prepared:

| X g | of N-heteroarylmethyl-1,3-diaminobenzene [coupler K1 to K4 of formula (I) as per Table 3] |
| U g | of developer E8 to E15 as per Table 2 |
| Y g | of coupler K11 to K36 as per Table 3 |
| Z g | of 6-chloro-2-ethylamino-4-nitrophenol (D2) |
| 10.0 g | of potassium oleate (8% aqueous solution) |
| 10.0 g | of ammonia (22% aqueous solution) |
| 10.0 g | of ethanol |
| 0.3 g | of ascorbic acid |
| to 100.0 g | water |

Just before use, 30 g of the foregoing coloring solution was mixed with 30 g of a 6% aqueous solution of hydrogen peroxide. The mixture was then applied to bleached hair. After an exposure time of 30 min at 40° C., the hair was rinsed with water, washed with a commercial shampoo and dried. Table 4 shows the coloring results.

Examples 39 to 62

Hair Colorants
Dye carriers in cream form and having the following composition were prepared:

| X g | of N-heteroarylmethyl-1,3-diaminobenzene (coupler K1 to K4 of formula (I) as per Table 3) |
| U g | of developer E8 to E15 as per Table 2 |
| Y g | of coupler K11 to K36 as per Table 3 |
| Z g | of 6-chloro-2-ethylamino-4-nitrophenol (D2) |
| 15.0 g | of cetyl alcohol |
| 0.3 g | of ascorbic acid |
| 3.5 g | of sodium lauryl alcohol diethylene glycol ether sulfate, 28% aqueous solution |
| 3.0 g | of ammonia, 22% aqueous solution |
| 0.3 g | of sodium sulfite, anhydrous |
| to 100 g | water |

Just before use, 30 g of the foregoing coloring cream was mixed with 30 g of a 6% solution of hydrogen peroxide. The mixture was then applied to the hair. After an exposure time of 30 min at 40° C., the hair was rinsed with water, washed with a commercial shampoo and dried. The coloring results are presented in Table 5.

TABLE 2

Developers

| E8 | 1,4-diaminobenzene |
| E9 | 2,5-diaminophenylethanol sulfate |
| E10 | 3-methyl-4-aminophenol |
| E11 | 4-amino-2-aminomethylphenol.2 HCl |
| E12 | 4-aminophenol |
| E13 | N,N-bis(2'-hydroxyethyl)-p-phenylenediamine sulfate |
| E14 | 4,5-diamino-1-(2'-hydroxyethyl)pyrazole sulfate |
| E15 | 2,5-diaminotoluene sulfate |

TABLE 3

Couplers

| K1 | N-thiophen-2-ylmethyl-1,3-diaminobenzene.HCl |
| K2 | N-furan-2-ylmethyl-1,3-diaminobenzene.HCl |
| K3 | 2-{4-amino-2-[(thiophen-2-ylmethyl)amino]-phenoxy}ethanol.HCl |
| K4 | 2-{4-amino-2-[(furan-2-ylmethyl)amino]-phenoxy}ethanol.HCl |
| K11 | 1,3-diaminobenzene |
| K12 | 2-amino-4-(2'-hydroxyethyl)aminoanisole sulfate |
| K13 | 1,3-diamino-4-(2'-hydroxyethoxy)benzene sulfate |
| K14 | 2,4-diamino-5-fluorotoluene sulfate |
| K15 | 3-amino-2-methylamino-6-methoxypyridine |
| K16 | 3,5-diamino-2,6-dimethoxypyridine.2 HCl |
| K17 | 2,4-diamino-5-ethoxytoluene sulfate |
| K18 | N-(3-dimethylamino)phenylurea |
| K19 | 1,3-bis(2,4-diaminophenoxy)propane.4 HCl |
| K21 | 3-aminophenol |
| K22 | 5-amino-2-methylphenol |
| K23 | 3-amino-2-chloro-6-methylphenol |
| K24 | 5-amino-4-fluoro-2-methylphenol sulfate |
| K25 | 1-naphthol |
| K26 | 1-acetoxy-2-methylnaphthalene |
| K31 | 1,3-dihydroxybenzene |
| K32 | 2-methyl-1,3-dihydroxybenzene |
| K33 | 1-chloro-2,4-dihydroxybenzene |
| K34 | 4-(2'-hydroxyethyl)amino-1,2-methylenedioxy-benzene.HCl |
| K35 | 3,4-methylenedioxyphenol |
| K36 | 2-amino-5-methylphenol |

TABLE 4

Hair Colorants

| Dyes | Example No. | | | | | |
|---|---|---|---|---|---|---|
| | 15 | 16 | 17 | 18 | 19 | 20 |
| | (Dyes in grams) | | | | | |
| K1 | 0.1 | 0.12 | 0.05 | 0.07 | 0.10 | 0.12 |
| E8 | 0.30 | | | | | |
| E9 | | | | | 0.25 | 0.30 |
| E15 | | 0.25 | 0.30 | 0.25 | | |
| K12 | | | 0.05 | | | |
| K13 | | | | 0.05 | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Dyeing result | blond | blond | blond | blond | blond | blond |

| Dyes | Example No. | | | | | |
|---|---|---|---|---|---|---|
| | 21 | 22 | 23 | 24 | 25 | 26 |
| | (Dyes in grams) | | | | | |
| K2 | 0.10 | 0.12 | 0.05 | 0.07 | 0.10 | 0.12 |
| E8 | 0.30 | | | | | |
| E9 | | | | | 0.25 | 0.30 |
| E15 | | 0.25 | 0.30 | 0.25 | | |
| K12 | | | 0.05 | | | |
| K13 | | | | 0.05 | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Dyeing result | blond | blond | blond | blond | blond | blond |

| Dyes | Example No. | | | | | |
|---|---|---|---|---|---|---|
| | 27 | 28 | 29 | 30 | 31 | 32 |
| | (Dyes in grams) | | | | | |
| K3 | 0.10 | 0.12 | 0.05 | 0.07 | 0.10 | 0.12 |
| E8 | 0.30 | | | | | |
| E9 | | | | | 0.25 | 0.30 |
| E15 | | 0.25 | 0.30 | 0.25 | | |
| K12 | | | 0.05 | | | |
| K13 | | | | 0.05 | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Dyeing result | blond | blond | blond | blond | blond | blond |

| Dyes | Example No. | | | | | |
|---|---|---|---|---|---|---|
| | 33 | 34 | 35 | 36 | 37 | 38 |
| | (Dyes in grams) | | | | | |
| K4 | 0.1 | 0.12 | 0.05 | 0.07 | 0.10 | 0.12 |
| E8 | 0.30 | | | | | |
| E9 | | | | | 0.25 | 0.30 |
| E15 | | 0.25 | 0.30 | 0.25 | | |
| K12 | | | 0.05 | | | |
| K13 | | | | 0.05 | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Dyeing result | blond | blond | blond | blond | blond | blond |

TABLE 5

Hair Colorants

| Dyes | Example No. | | | | | |
|---|---|---|---|---|---|---|
| | 39 | 40 | 41 | 42 | 43 | 44 |
| | (Dyes in grams) | | | | | |
| K1 | 0.60 | 1.30 | 1.15 | 0.15 | 0.15 | 0.15 |
| E8 | 1.50 | | | | | |
| E13 | | 1.60 | | | | 0.70 |
| E15 | | | 1.80 | 0.70 | 0.70 | |
| K12 | 0.60 | | | | | |
| K31 | 1.10 | 1.10 | 1.10 | 0.40 | 0.40 | 0.40 |
| D2 | | | | 0.10 | 0.10 | 0.10 |
| K23 | | | 0.05 | 0.10 | 0.10 | 0.10 |
| Dyeing result | black | black | black | brown | brown | brown |

| Dyes | Example No. | | | | | |
|---|---|---|---|---|---|---|
| | 45 | 46 | 47 | 48 | 49 | 50 |
| | (Dyes in grams) | | | | | |
| K2 | 0.60 | 1.30 | 1.15 | 0.15 | 0.15 | 0.15 |
| E8 | 1.50 | | | | | |
| E13 | | 1.60 | | | | 0.70 |
| E15 | | | 1.80 | 0.70 | 0.70 | |
| K12 | 0.60 | | | | | |
| K31 | 1.10 | 1.10 | 1.10 | 0.40 | 0.40 | 0.40 |
| D2 | | | | 0.10 | 0.10 | 0.10 |
| K23 | | | 0.05 | 0.10 | 0.10 | 0.10 |
| Dyeing result | black | black | black | brown | brown | brown |

| Dyes | Example No. | | | | | |
|---|---|---|---|---|---|---|
| | 51 | 52 | 53 | 54 | 55 | 56 |
| | (Dyes in grams) | | | | | |
| K3 | 0.60 | 1.30 | 1.15 | 0.15 | 0.15 | 0.15 |
| E8 | 1.50 | | | | | |
| E13 | | 1.60 | | | | 0.70 |
| E15 | | | 1.80 | 0.70 | 0.70 | |
| K12 | 0.60 | | | | | |
| K31 | 1.10 | 1.10 | 1.10 | 0.40 | 0.40 | 0.40 |
| D2 | | | | 0.10 | 0.10 | 0.10 |
| K23 | | | 0.05 | 0.10 | 0.10 | 0.10 |
| Dyeing result | black | black | black | brown | brown | brown |

| Dyes | Example No. | | | | | |
|---|---|---|---|---|---|---|
| | 57 | 58 | 59 | 60 | 61 | 62 |
| | (Dyes in grams) | | | | | |
| K4 | 0.60 | 1.30 | 1.15 | 0.15 | 0.15 | 0.15 |
| E8 | 1.50 | | | | | |
| E13 | | 1.60 | | | | 0.70 |
| E15 | | | 1.80 | 0.70 | 0.70 | |
| K12 | 0.60 | | | | | |
| K31 | 1.10 | 1.10 | 1.10 | 0.40 | 0.40 | 0.40 |
| D2 | | | | 0.10 | 0.10 | 0.10 |
| K23 | | | 0.05 | 0.10 | 0.10 | 0.10 |
| Dyeing result | black | black | black | brown | brown | brown |

What is claimed is:

1. An agent for oxidative dyeing of keratin fibers, said agent containing at least one developer and at least one coupler, wherein said at least one coupler is at least one N-heteroarylmethyl-m-phenylenediamine derivative of formula (I), or a salt thereof with an organic or inorganic acid,

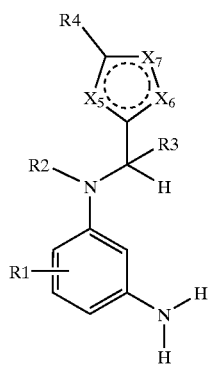

(I)

wherein X5 denotes sulfur, nitrogen, oxygen, C—R6 or N—R5;
X6 denotes sulfur, nitrogen, oxygen, C—R7 or N—R5;
X7 denotes sulfur, nitrogen, oxygen, C—R8 or N—R5;
R1 denotes hydrogen, a $C_1$–$C_4$-alkyl group, a $C_1$–$C_4$-hydroxyalkoxy group or a $C_1$–$C_4$-hydroxyalkyl group;
R2 and R3 can be equal or different and independently of each other denote hydrogen or a $C_1$–$C_6$-alkyl group;
R4, R6, R7, R8 can be equal or different and independently of each other denote hydrogen, a halogen atom, a cyano group, a $C_1$–$C_4$-alkoxy group, a $C_1$–$C_6$-alkyl group, a $C_1$–$C_4$-alkyl thioether group, a mercapto group, a nitro group, an amino group, a $C_1$–$C_4$-alkylamino group, a di($C_1$–$C_4$)-alkylamino group, a di($C_1$–$C_4$-hydroxyalkyl)amino group, a $C_1$–$C_4$-hydroxyalkylamino group, a trifluoromethyl group, a —C(O)CH$_3$— group, a —C(O)CF$_3$ group, an —Si (CH$_3$)$_3$ group, a $C_1$–$C_4$-hydroxyalkyl group or a $C_3$–$C_4$ dihydroxyalkyl group; and R5 denotes hydrogen, a $C_1$–$C_6$-alkyl group, a $C_2$–$C_4$-hydroxyalkyl group, a phenyl group or an acetyl group; and
wherein at least one and at the most two of the X5 to X7 groups denote respectively C—R6 or C—R7 or C—R8 and at the most one of the X5 to X7 groups denote sulfur, oxygen or N—R5.

2. The agent according to claim 1, wherein R1 denotes said hydrogen or said $C_1$–$C_4$-hydroxyalkyl group, and wherein R2 and R3, or R2, R3 and R4, each denote said hydrogen.

3. The agent according to claim 1, wherein R1 denotes said hydrogen or said $C_1$–$C_4$-hydroxyalkyl group, R2 and R3, or R2, R3 and R4, each denote said hydrogen, X5 denotes said sulfur or said oxygen, X6 denotes said nitrogen or said C—R7 and X7 denotes said C—R8, and at least one of R7 and R8 denotes said hydrogen.

4. The agent according to claim 1, wherein R1 denotes said hydrogen or said $C_1$–$C_4$-hydroxyalkyl group, R2 and R3, or R2, R3 and R4, each denote said hydrogen, X7 denotes said sulfur or said oxygen, X5 denotes said C—R6 and X6 denotes said C—R7, and at least one of R6 and R7 denotes said hydrogen.

5. The agent according to claim 1, wherein R1 denotes said hydrogen or said $C_1$–$C_4$-hydroxyalkyl group, R2 and R3, or R2, R3 and R4, denote said hydrogen, X6 denotes said sulfur or said oxygen, X5 denotes said C—R6 and X7 denotes said C—R8, and at least one of R6 and R8 groups denotes said hydrogen.

6. The agent according to claim 1, wherein the at least one N-heteroaryl-methyl-m-phenylenediamine derivative of formula (I) is selected from the group consisting of N-thiophen-3-ylmethyl-1,3-diaminobenzene, N-furan-3-ylmethyl-1,3-diaminobenzene, N-furan-2-ylmethyl-1,3-diaminobenzene, N-thiopher-2-ylmethyl-1,3-diaminobenzene, 2-{4-amino-2-[(thiophen-3-ylmethyl)-amino]-phenoxy}ethanol, 2-{4-amino-2-[(thiophen-2-ylmethyl)amino]-phenoxy}-ethanol, 2-{4-amino-2-[(furan-3-ylmethyl)amino]phenoxy}ethanol, 2-{4-amino-2-[(furan-2-ylmethyl)amino]phenoxy}ethanol, 2-{2-amino-4-[(thiophen-2-ylmethyl)-amino]-phenoxy}ethanol and 2-{2-amino-4-[(furan-2-ylmethyl)amino]-phenoxy}-ethanol, or is a salt thereof.

7. The agent according to claim 1, containing from 0.005 to 20 weight percent of said at least one N-heteroarylmethyl-m-phenylenediamine derivative of said formula (I).

8. The agent according to claim 1, wherein the at least one developer is selected from the group consisting of 1,4-diaminobenzene, 1,4-diamino-2-methylbenzene, 1,4-diamino-2,6-dimethylbenzene, 1,4-diamino-3,5-diethyl-benzene, 1,4-diamino-2,5-dimethylbenzene, 1,4-diamino-2,3-dimethyl-benzen, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)benzene, 2,5-diaminobiphenyl, 1,4-diamino-2-methoxymethyl-benzene, 1,4-diamino-2-aminomethylbenzene, 1,4-diamino-2-hydroxymethyl-benzene, 1,4-diamino-2-(2-hydroxyethoxy)benzene, 1-(2,5-diaminophenyl)-ethanol, 2-[2-(acetylamino)-ethoxy)]-1,4-diaminobenzene, 4-phenylaminoaniline, 4-dimethylaminoaniline, 4-diethylaminoaniline, 4-dipropylaminoaniline, 4-[ethyl-(2-hydroxyethyl)amino]-aniline, 4-[di(2-hydroxyethyl)amino]aniline, 4-[di(2-hydroxyethyl)amino]-2-methylaniline, 4-[(2-methoxyethyl)amino]aniline, 4-[(3-hydroxypropyl)amino]-aniline, 4-[(2,3-dihydroxypropyl)amino]aniline, 1,4-diamino-2-(2-hydroxyethyl)-benzene, 1,4-diamino-2-(1-methylethyl)benzene, 1,3-bis-[(4-aminophenyl)-(2-hydroxyethyl)amino]-2-propanol, 1,4-bis-[(4-aminophenyl)amino]butane, 1,8-bis-(2,5-diaminophenoxy)-3,6-dioxaoctane, 4-aminophenol, 4amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[(2-hydroxyethyl)-amino]-methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 4,5-diamino-3-methyl-1-methyl-1H-pyrazole, 2-aminophenol, 2-amino-6-methylphenol and 2-amino-5-methylphenol.

9. The agent according to claim 1, further comprising at least one other coupler in addition to said at least one coupler.

10. The agent according to claim 1, further comprising at least one direct dye.

11. The agent according to claim 9, containing from 0.005 to 20 percent by weight of at total amount of said at least one developer, said at least one coupler and said at least one other coupler.

12. A ready-to-use colorant made by mixing an agent for oxidative dyeing of keratin fibers with an oxidant in a weight ratio of the agent to the oxidant of 5:1 to 1:3;

wherein said a gent of oxidative dyeing of keratin fibers contains at least one developer and al least one coupler; and wherein said at least one coupler comprises at least one N-heteroarylmethyl-m-phenylenediamine derivative of formula (I), or a salt thereof with an organic or inorganic acid,

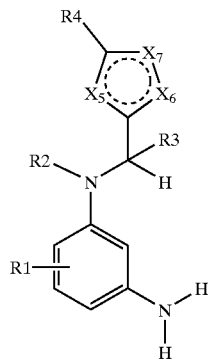
(II)

wherein X5 denotes sulfur, nitrogen, oxygen, C—R6 or N—R5;

X6 denotes sulfur, nitrogen, oxygen, C—R7 or N—R5;

X7 denotes sulfur, nitrogen, oxygen, C—R8 or N—R5;

R1 denotes hydrogen, a $C_1$–$C_4$-alkyl group, a $C_1$–$C_4$-hydroxyalkoxy group or a $C_1$–$C_4$-hydroxyalkyl group;

R2 and R3 can be equal or different and independently of each other denote hydrogen or $C_1$–$C_6$-alkyl group;

R4, R6, R7, R8 can be equal or different and independently of each other denote hydrogen, a halogen atom, a cyano group, a $C_1$–$C_4$-alkoxy group, a $C_1$–$C_6$-alkyl group, a $C_1$–$C_4$-alkyl thioether group, a mercapto group, a nitro group, an amino group, a$C_1$–$C_4$-alkylamino group, a di($C_1$–$C_4$)-alkylamino group, a di($C_1$–$C_4$-hydroxyalkyl)amino group, a $C_1$–$C_4$-hydroxyalkylamino group, a trifluoromethyl group, a —C(O)CH$_3$— group, a —C(O)CF$_3$ group, an —Si(CH$_3$)$_3$ group, a $C_1$–$C_4$-hydroxyalkyl group or a $C_3$–$C_4$ dihydroxyalkyl group; and R5 denotes hydrogen, a $C_1$–$C_6$-alkyl group, $C_1$–$C_4$-hydroxyalkyl group, a phenyl group or an acetyl group; and wherein at least one and at the most two of the X5 to X7 groups denote respectively C—R6 or C—R7 or C—R8 and at the most one of the X5 to X7 groups denote sulfur, oxygen or N—R5.

13. The ready-to-use colorant as defined in claim 12, having a pH of 3 to 11.5.

14. The ready-to-use colorant as defined in claim 12, consisting of a hair colorant.

15. A heteroarylmethyl-m-phenylenediamine derivative of formula (II), or a water-soluble salt thereof with an organic or an inorganic acid,

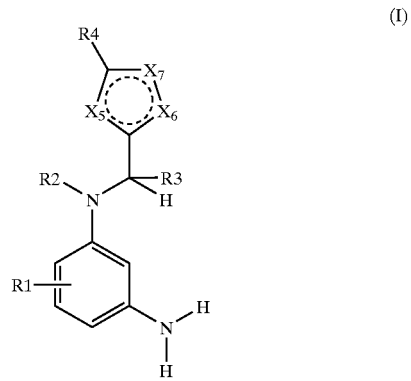
(I)

wherein X5 denotes sulfur, nitrogen, oxygen, C—R6 or N—R5;

X6 denotes sulfur, nitrogen, oxygen, C—R7 or N—R5;

X7 denotes sulfur, nitrogen, oxygen, C—R8 or N—R5;

R1 denotes hydrogen, a $C_1$–$C_4$-alkyl group, a $C_1$–$C_4$-hydroxyalkoxy group or a $C_1$–$C_4$-hydroxyalkyl group;

R2 and R3 can be equal or different and independently of each other denote hydrogen or a $C_1$–$C_6$-alkyl group;

R4, R6, R7, R8 can to equal or different and independently of each other denote hydrogen, a halogen atom, a cyano group, a $C_1$–$C_4$-alkoxy group, a $C_1$–$C_6$-alkyl group, a $C_1$–$C_4$-alkyl thioether group, a mercapto group, a nitro group, an amino group, a $C_1$–$C_4$-alkylamino group, a di($C_1$–$C_4$)-alkylamino group, a di($C_1$–$C_4$-hydroxyalkyl)amino group, a $C_1$–$C_4$-hydroxyalkylamino group, a trifluoromethyl group, a —C(O)CH$_3$— group, a —C(O)CF$_3$ group, an —Si(CH$_3$)$_3$ group, a $C_1$–$C_4$-hydroxyalkyl group or a $C_1$–$C_4$ dihydroxyalkyl group; and R5 denotes hydrogen, a $C_1$–$C_6$-alky group, a $C_1$–$C_4$-hydroxyalkyl group, a phenyl group or an acetyl group; and wherein at least one and at the most two of the X5 to X7 groups denote respectively C—R6 or C—R7 or C—R8 and at the most one of the X5 to X7 groups denote sulfur, oxygen or N—R5;

provided that at least one of the R1, R2, R3, R4, R6, R7 and R8 groups does not denote said hydrogen when X5 or X6 denotes said sulfur.

* * * * *